United States Patent [19]

Schmitt

[11] Patent Number: 5,779,691
[45] Date of Patent: Jul. 14, 1998

[54] FASTENING TAPE FOR A SANITARY ARTICLE PARTICULARLY DISPOSABLE DIAPER

[75] Inventor: Achim Schmitt, Munster-Sarmsheim, Germany

[73] Assignee: The Procter & Gamble Company, Cincinnati, Ohio

[21] Appl. No.: 809,684

[22] PCT Filed: Sep. 1, 1995

[86] PCT No.: PCT/US95/11166

§ 371 Date: Mar. 27, 1997

§ 102(e) Date: Mar. 27, 1997

[87] PCT Pub. No.: WO96/10382

PCT Pub. Date: Apr. 11, 1996

[30] Foreign Application Priority Data

Sep. 30, 1994 [EP] European Pat. Off. .............. 94115429

[51] Int. Cl.[6] .................. A61F 13/56; B32B 31/18; C09J 7/04
[52] U.S. Cl. .................. 604/386; 604/389; 428/40; 428/99; 428/100; 428/152; 428/176; 428/343; 428/913; 156/73.1; 156/73.4; 156/183; 156/210; 156/250

[58] Field of Search ................ 604/385.1, 385.2, 604/386, 389, 390, 391; 428/40, 99, 100, 152, 176, 343, 913; 156/73.1, 73.4, 183, 210, 250

[56] References Cited

U.S. PATENT DOCUMENTS

| | | | |
|---|---|---|---|
| 4,158,363 | 6/1979 | Schaar | 604/390 |
| 4,522,853 | 6/1985 | Szonn et al. | 428/40 |
| 4,743,242 | 5/1988 | Grube et al. | 604/389 |
| 4,787,897 | 11/1988 | Torimae et al. | 604/389 |
| 4,857,067 | 8/1989 | Wood et al. | 604/389 |
| 5,092,862 | 3/1992 | Muckenfuhs et al. | 604/389 X |

Primary Examiner—Mary Beth Jones
Attorney, Agent, or Firm—Theodore P. Cummings; Steven W. Miller; Jacobus C. Rasser

[57] ABSTRACT

A fastening tape for a sanitary article, for fastening the article on the body of a person is attached to the article at one of its end portions (18) and provided with any fastener (22) on one surface of the other end portion (20). A stretchable elastic portion (30) consists of a sandwich structure of a tape section (32) of a stretchable elastic material secured to one surface of the fastening tape (10) at least at both ends (32a, 32b) thereof, to bridge a section of the fastening tape (10).

11 Claims, 3 Drawing Sheets

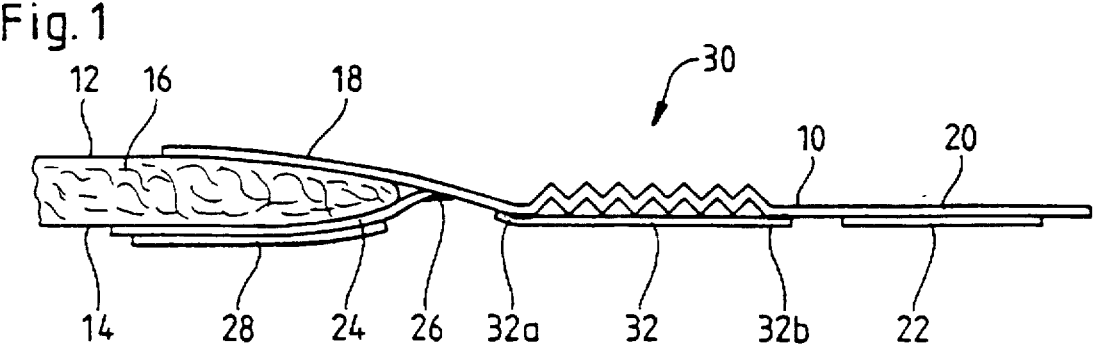
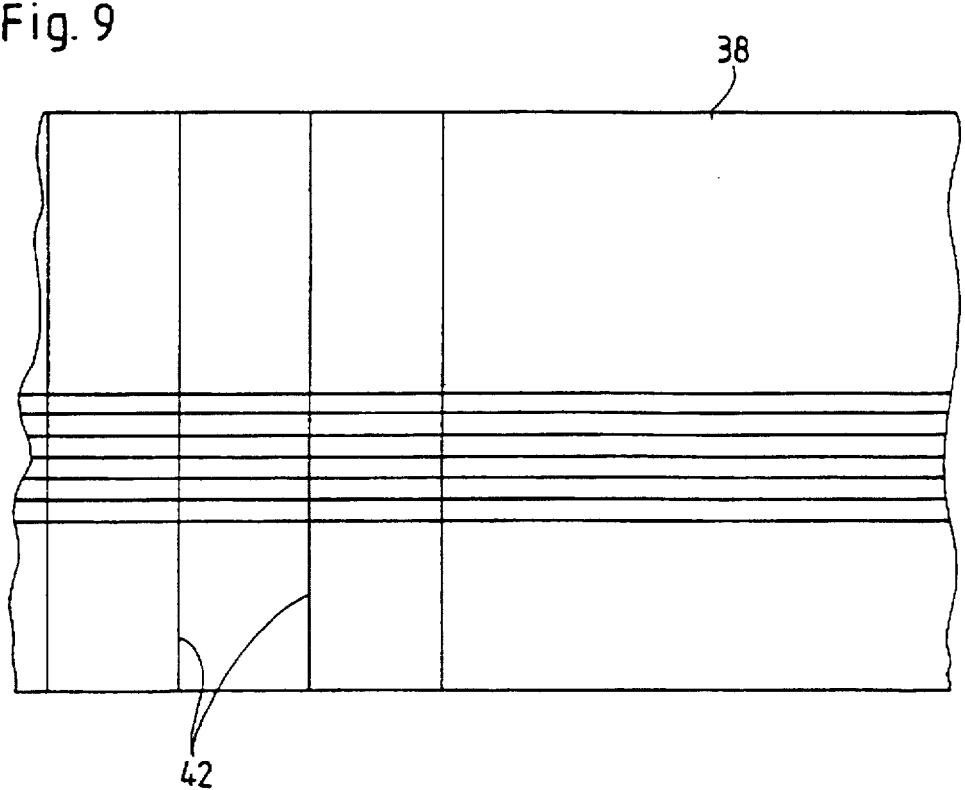

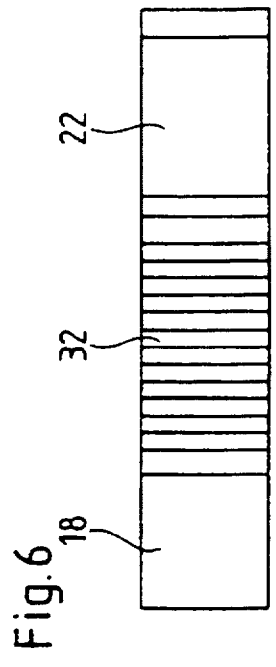
Fig.2
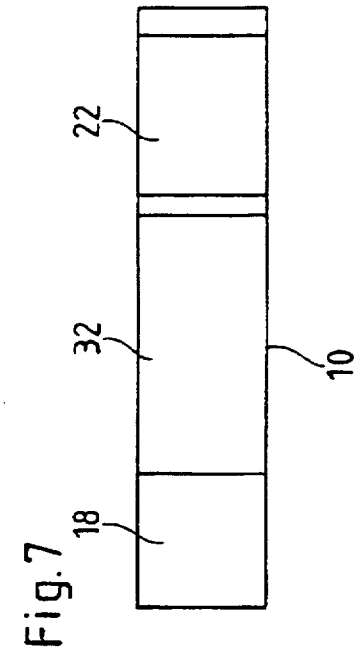
Fig.3
Fig.4
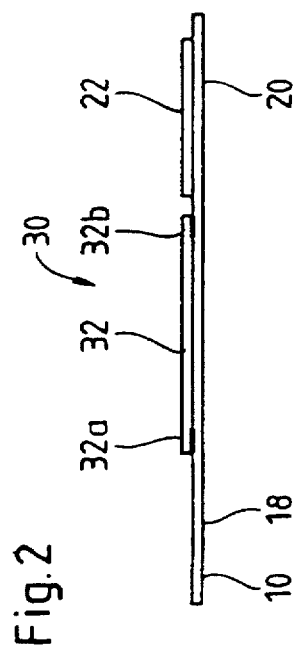
Fig.5
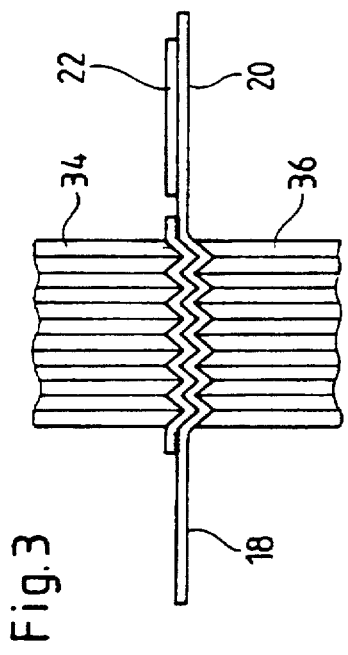
Fig.6
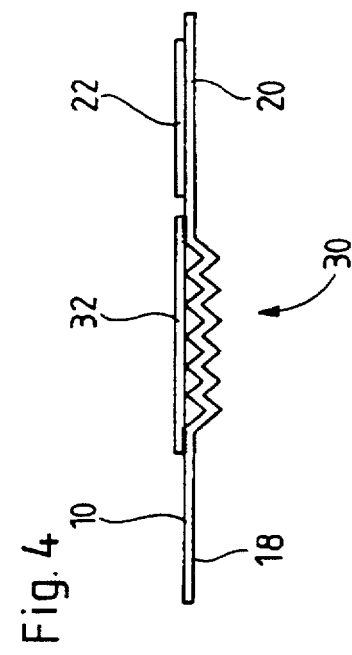
Fig.7

FASTENING TAPE FOR A SANITARY ARTICLE PARTICULARLY DISPOSABLE DIAPER

The invention relates to a fastening tape for a sanitary article, particularly disposable diaper, for fastening of the article on the body of a person, the fastening tape being attached to the article at one of its end portions and being provided with a fastening means on one surface of the other end portion, a stretchable elastic portion being provided between the end portions. The invention further relates to a method for producing the fastening tape.

Conventional sanitary articles like disposable diapers are provided with fastening tapes attached to the diaper and provided with a layer of pressure-sensitive adhesive at the end portion thereof. The tapes are used to close the diaper round the wearer's body and to fasten the diaper on the body. Among these fastening tapes, there have also been elastically stretchable tapes to improve the fit and the comfort of the articles.

However, if the part of the tapes covered by the adhesive layer is stretchable as disclosed by the U.S. Pat. No. 4,063, 559 or the EP-A1 0 191 355, the tape may be inadvertently released by peeling off under a predetermined stress. Other conventional stretchable fastening tapes as disclosed by the EP-A2 0 249 073 or the EP-A1 0 487 758 consist of stretchable and non-stretchable portions being connected in the longitudinal direction end to end or by overlapping. In these cases, providing of a reliable connection between the portions under industrial conditions with acceptable costs has not yet been possible.

On the other hand, it is not easy to exactly achieve a predetermined elasticity of the tapes. If the forces necessary to stretch the tape exceed a certain limit, there will be no effect and the wearing comfort will not be improved. On the other hand, if the tape is too soft, over-stretching of the tape may occur by which the diaper may get loose or even open.

Thus it is the main object of the invention to provide a fastening tape for a sanitary article useful for the wearing comfort of the article by a comparably soft resiliency without the risk of over-stretching of the tape.

Moreover, it is an object of the invention to provide a tape of the above kind which can be easily manufactured at low costs, and a method of producing the tape accordingly.

To comply with this object, a fastening tape according to the present invention is characterized in that a tape section of a stretchable elastic material is secured to the fastening tape at least at both ends thereof, to bridge a non-linear section of the fastening tape which is longer than the-stretchable elastic tape section.

Thus the invention provides a combination of an elastic tape, to improve wearing comfort of the article in question, and a non-elastic tape which has a kind of stop function determining the maximum extension of the elastic section to avoid rupture thereof.

The tape section of stretchable elastic material may be secured to the fastening tape at the ends of the elastic material only or along the whole length of the elastic tape or in integrals. Securing the elastic tape in intervals will be particularly suitable in case the section of the fastening tape bridged by the elastic tape achieves a zigzag-folding by a suitable die, particularly by ringrolling. In this case, the vallies of the zigzag-shape may be secured to the elastic tape. Securing the tapes in intervals may be realized by an adhesive or also by different types of welding methods.

In any case, the length of the fastening tape bridged by the elastic tape must be longer than the elastic tape in the relaxed length. In this position the foldings will appear and will make sure that the fastening tape does not deform away from the elastic tape. On the other hand, if the elastic tape is stretched into a predetermined position, the fastening tape will be extended to the straight position thereof where the zigzag-form disappears.

Preferably, foldings are formed in the portion of the fastening tape bridged by the elastic tape section which disappear more and more when the elastic tape section is stretched.

If the laminate formed by the fastening tape and the elastic tape section is ringrolled or deformed by any other pair of dies having a zigzag-shaped gab, the laminate will stretch. After being removed from the dies, the elastic tape will return to its non-stretched position while the zigzag-shaped deformation of the fastening tape will remain. Another possibility to obtain the combination of the fastening tape and the elastic tape would be to secure the elastic tape to the fastening tape in a pre-stressed condition. In this case, when the elastic tape section is released, the corresponding part of the fastening tape will be longer than the elastic tape and will deform, for example in a zig-zag-shape in case both tapes are connected in intervals. Both possibilities, i.e. a zig-zag die deformation and securing the elastic tape section in a prestressed condition, may be combined with each other.

The material of the stretchable elastic tape section may be natural rubber or synthetic rubber or any comparable elastomeric material. According to tests the Inventor has made, a stretchability of 2 mm/N appeared to be acceptable.

The material of the fastening tape is more or less non-stretchable and non-elastic under the conditions the fastening tape is used in the present context. The material thereof should be deformable as the fastening tapes used for applicants present products, for instance diapers sold under the trademark Pampers.

Embodiments of the invention will be described with reference to the enclosed drawings which are not intended to limit the scope of the invention.

FIG. 1 is a cross-section of the edge portion of a diaper being provided with a fastening tape according to the invention;

FIG. 2 shows a side view of the first step in the method for producing an elastically stretchable portion of the tape;

FIG. 3 shows a side view of the second step in the method for producing an elastically stretchable portion of the tape;

FIG. 4 shows a side view of the third step in the method for producing an elastically stretchable portion of the tape;

FIG. 5 shows a top view of the tape corresponding to the step shown in FIG. 2;

FIG. 6 shows a top view of the tape corresponding to the step shown in FIG. 3;

FIG. 7 shows a top view of the tape corresponding to the step shown in FIG. 4;

FIG. 9 is a top view on the web achieved by ringrolling.

Figure 8:
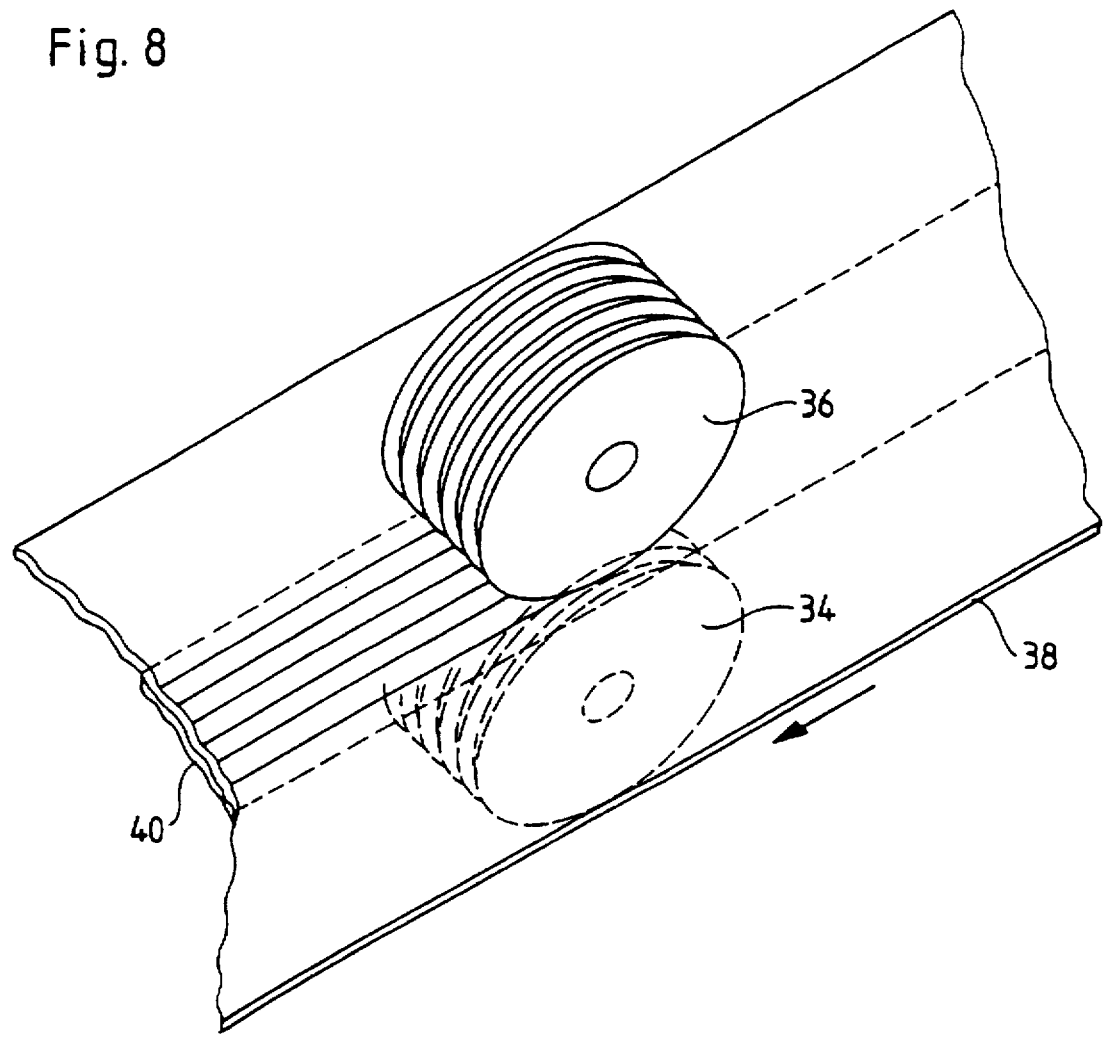
FIG. 8 is a perspective view, in larger scale, of a ringrolling step for forming the elastically stretchable portion of the tape.

In the following description of embodiments, a diaper will be used as an example for a sanitary article according to the invention. It should be noted that it is not intended to limit the use of the fastening tape according to the invention to diapers. The fastening tape according to the invention is applicable to other disposable sanitary articles which are to be attached to the body of the wearer as well.

FIG. 1 is a cross-section through the edge of a diaper being provided with a fastening tape 10 according to the invention. The diaper comprises a liquid-impermeable backsheet 12, a liquid-permeable topsheet 14 to face the skin of the wearer and an absorbent core 16 between both.

An end portion 18 of the fastening tape 10 is adhered to the edge portion of the backsheet 12, usually by a hot melt adhesive, while the other end portion 20 of the fastening tape on the right side in FIG. 1 is provided with an adhesive layer 22 of a pressure-sensitive adhesive for closing the diaper in the well-known way. Another adhesive tape 24 is adhered to the edge portion of the topsheet 14 and provided with a projecting end 26 adhered to the lower surface of the fastening tape 10 in FIG. 1. The lower surface of the adhesive tape 24 is covered by a release layer 28 to which the adhesive layer 22 at the end portion 20 of the fastening tape is preliminary attached before fixing the diaper on a wearer.

A diaper having fastening tapes of this kind is well-known in the art and does not require any further description.

According to the invention, the fastening tape 10 comprises an elastically stretchable center portion 30 between the end portions 18,20. The center portion 30 will be described in detail with reference to FIG. 1 in connection with FIGS. 2 to 7. FIGS. 2 to 4 show the fastening tape in an upside down orientation compared with FIG. 1. The same reference numerals have been used as in FIG. 1 to designate identical or corresponding members.

The elastically stretchable, central portion 30 is formed by a laminate consisting of the fastening tape 10 and a tape section 32 of an elastic material adhered to the fastening tape with its end portions 32a,32b, to bridge the fastening tape 10 over a certain length thereof. The corresponding top view is shown in FIG. 5.

As shown in FIGS. 3 and 6, the laminate consisting of the central portion of the fastening tape 10 and the tape section 32 of elastic material is passed through the gap of a pair of two meshing rolls having saw-tooth shaped corresponding surfaces the ridges of which extend circumferentially. This method is frequently designated as "ringrolling".

If the laminate formed by the fastening tape 10 and the elastic tape section 32 is moved through the gap of these rolls which have been shown in part in FIG. 3 and designated by 34 and 36, both of the layers 10,32 are stretched zigzag-wise. Since the tape section 32 is elastic, the stretch will be recovered after leaving the rolls 34,36, while the material of the fastening tape 10 is not elastic and thus the fastening tape will remain fan-folded in the portion 30, as shown in FIG. 4.

Thus, if a stretching force is exerted to the portion 30, the tape section 32 of elastic material will elastically stretch while the corresponding portion of the fastening tape 10 is extended to a straight form in which no further extension of the elastically stretchable portion 30 is possible. The portion of the fastening tape 10 bridged by the elastic tape section 32 thus forms a kind of stop determining the end position of the stretch of the elastic tape section.

The fastening tape 10 may be cut from an endless web 38 shown in a perspective view in FIGS. 8 and 9.

According to FIGS. 8 and 9, a web 38 having a width corresponding to the length of the fastening tape 10, is passed lengthwise through the pair of intermeshing rolls 34,36. A tape 40 of an elastic material is adhered to the lower surface of the web 38 which is not seen in FIGS. 8 and 9. This tape 40 covers the lower surface of the web 38 over a width slightly extending beyond the track of the lower roll 34 on both sides, as may be taken from FIG. 8. When passing the gap of the rolls 34,36, the laminate consisting of the web 38 and the tape 40 is experiencing the folding process described in connection with FIGS. 3 and 6. Before or after this ringrolling step, a strip of a pressure sensitive adhesive may be applied to the web 38 to the surface not visible in FIGS. 8 and 9, to form the adhesive layer 22 on the lower side of the fastening tape 10 shown in FIG. 1. Finally, the web 38 is cut by cutting lines 42 as shown in FIG. 9, to form fastening tapes 10 according to FIG. 1.

What is claimed is:

1. Fastening device for a sanitary article for fastening the article onto a wearer's body, the fastening device comprising a fastening tape having two end portions and being attached to the sanitary article at one of its end portions (18) and being provided with a fastening means (22) on one surface of the other end portion (20); and a stretchable elastic portion (30) being provided between the end portions, characterized in that a tape section (32) of a stretchable elastic material is secured to a length of the fastening tape (10) at least at both ends (32a, 32b) of the tape section; the length of the fastening tape that is located between the two ends of the elastic tape section exceeds the length of the elastic tape section, thereby forming said stretchable elastic portion of the fastening tape.

2. Fastening device according to claim 1, characterized in that foldings are formed in said stretchable elastic portion (30) of the fastening tape (10) which lies between the ends of the elastic tape section (32), the foldings extending laterally with respect to the length of the fastening tape.

3. Fastening device according to claim 1, characterized in that the ends (32a,32b) of the elastic tape section (32) are secured to the fastening tape (10) by an adhesive.

4. Fastening device according to claim 1, characterized in that the ends (32a,32b) of the elastic tape section (32) are secured to the fastening tape (10) by welding including heat welding and ultrasonic welding.

5. Fastening device according to claim 1, characterized in that the fastening means (22) is formed by an adhesive layer on one surface of the other end portion (20) of the fastening tape.

6. Fastening device according to claim 1, characterized in that the fastening means (22) is formed by mechanical fastening means including Velcro tapes, hooks, buttons and the like.

7. Fastening device as claimed in claim 1, characterized in that the tape section (32) of said stretchable elastic material is secured to the fastening tape section (10) in intervals between the ends (32a,32b) of the tape section of elastic material.

8. Method for manufacturing a fastening device according to one of claims 1 to 8, characterized in that the elastic tape section (32) is secured at least at the ends (32a,32b) thereof to the fastening tape to bridge a central portion of the fastening tape, and that a laminate comprising the fastening tape and the elastic tape section is inserted into a zigzag-shaped gap of two dies.

9. Method for manufacturing a fastening device according to claim 8, characterized in that an elongated web (38) is provided with a tape (40) of an elastic material which is secured to the web in the longitudinal direction thereof (38) by adhering at least the lateral edges of the tape to one surface of the web (38), forming said laminate and that said laminate is ringrolled, after which fastening tapes are formed by cutting the web laterally.

10. Method as claimed in claim 9, characterized in that the tape section of said stretchable elastic material is secured to the fastening tape in intervals between the both ends (32a, 32b) of the elastic taped section.

11. Method as claimed in one of claim 9, characterized in that dies for deforming the laminate of the fastening tape and the elastic tape section are formed by ringrolls.

* * * * *